(12) United States Patent
Oppegard et al.

(10) Patent No.: US 11,083,827 B2
(45) Date of Patent: Aug. 10, 2021

(54) MEDICAL FLUID THERAPY MACHINE INCLUDING SERVICING REGIME THEREFORE

(71) Applicant: Baxter International Inc., Deerfield, IL (US)

(72) Inventors: Shawn Collin Oppegard, Fox River Grove, IL (US); Marc Alexander Barten, Chicago, IL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 422 days.

(21) Appl. No.: 15/688,062

(22) Filed: Aug. 28, 2017

(65) Prior Publication Data

US 2018/0093027 A1    Apr. 5, 2018

Related U.S. Application Data

(60) Provisional application No. 62/403,568, filed on Oct. 3, 2016.

(51) Int. Cl.
*A61M 1/16* (2006.01)
*G16H 40/40* (2018.01)
(Continued)

(52) U.S. Cl.
CPC ............ *A61M 1/1601* (2014.02); *A61M 1/28* (2013.01); *A61M 1/342* (2013.01);
(Continued)

(58) Field of Classification Search
CPC ........ A61M 1/601; A61M 1/28; A61M 1/342; A61M 1/3643; A61M 2205/12; A61M 2205/273; A61M 2205/3303; A61M 2205/3334; A61M 2205/3368; A61M 2205/3553; A61M 2205/3576; A61M 2205/50; A61M 1/1601; G06F 19/3468; G06Q 50/22; G16H 20/40; G16H 40/40
See application file for complete search history.

(56) References Cited

U.S. PATENT DOCUMENTS 5,629,871 A * 5/1997 Love .................. A61M 1/16
702/34
8,177,704 B1 * 5/2012 Mohl .................. A61B 5/6859
600/16

OTHER PUBLICATIONS

Office Action issued in related European Patent Application No. 17785137.5-1126 dated May 24, 2019—3 pages.

* cited by examiner

*Primary Examiner* — Tiffany Legette
(74) *Attorney, Agent, or Firm* — K&L Gates LLP

(57) ABSTRACT

A medical fluid delivery system includes: a medical fluid delivery machine including a component having at least one of associated output data or associated test data; at least one of a (i) component output replacement limit and a component output soft limit for the component or (ii) a component testing replacement limit or a component testing soft limit for the component; and a computer programmed to store at least one of (i) or (ii), and for (i) analyze the output data to provide a first indication of how well the component is performing relative to the component output replacement limit and the component output soft limit, and for (ii) analyze the test data to provide a second indication of how well the at least one component is testing relative to the component testing replacement limit and the component testing soft limit.

25 Claims, 8 Drawing Sheets

(51) Int. Cl.
*A61M 1/28* (2006.01)
*A61M 1/34* (2006.01)
*A61M 1/36* (2006.01)
(52) U.S. Cl.
CPC .......... *A61M 1/3643* (2013.01); *G16H 40/40* (2018.01); *A61M 2205/12* (2013.01)

Service Mode - Components at Soft Limit for 9/28/16

122, 126, 132, 216

| Item | Component | Location | Replacement # | Uses/Hours Remaining | Projected Date to Fail | See Graph |
|---|---|---|---|---|---|---|
| 1 | pressure sensor | fresh dialysis inlet | 123456 | 3 treatments | 9/30/16 | ∿ |
| 2 | pressure sensor | blood outlet | 234567 | 4 treatments | 10/1/16 | ∿ |
| 3 | binary valve pneumatic | bicarb inlet | 345678 | 6 treatments | 10/4/16 | ∿ |
| 4 | variable valve pneumatic | blood pump | 456789 | 6 treatments | 10/4/16 | ∿ |
| 5 | ultrafilter | dialysis circuit | 567890 | 7 treatments | 10/5/16 | ∿ |

[ Ultrafilter Trends ] 246  [ Dialyzer Trends ] 248  [ Pressure Sense Trends ] 250  [ Pneumatic Valve Trends ] 252

Service Mode - Machines at Soft Limit for 9/28/16

| Item | Location | Machine Identity | # of Components at Soft Limit | Uses/Hours Remaining | Projected Date of Failure |
|---|---|---|---|---|---|
| 1 | P. Shent | HD017 | 1 | 3 treatments | 9/30/16 |
| 2 | Ft. Myers | HD009 | 1 | 3 treatments | 9/30/16 |
| 3 | Miami | CRRT005 | 1 | 4 treatments | 10/1/16 |
| 4 | Orlando | PD007 | 2 | 4 treatments | 10/1/16 |
| 5 | J. Doe | PD010 | 1 | 4 treatments | 10/1/16 |
| 6 | Jacksonville | LVP006 | 3 | 5 treatments | 10/3/16 |
| 7 | Tampa | HD008 | 1 | 5 treatments | 10/3/16 |
| 8 | Tampa | LVP001 | 1 | 5 treatments | 10/3/16 |
| 9 | Orlando | PD040 | 2 | 5 treatments | 10/3/16 |
| 10 | Jacksonville | PD018 | 1 | 5 treatments | 10/3/16 |

[ Ultrafilters Averaged ] 256    [ Dialyzers Averaged ] 258    [ Reorder Now ] 260

244

FIG. 7

MEDICAL FLUID THERAPY MACHINE INCLUDING SERVICING REGIME THEREFORE

PRIORITY CLAIM

This application claims priority to and the benefit of U.S. Provisional Application No. 62/403,568, entitled "Medical Fluid Therapy Machine Including Servicing Regime Therefore", filed Oct. 3, 2016, the entire contents of which are incorporated herein by reference and relied upon.

BACKGROUND

The present disclosure relates generally to devices, systems and methods for medical fluid delivery machines. More specifically, the present disclosure relates to the servicing of components used in medical fluid delivery machines, such as renal failure therapy machines.

Regarding renal failure therapy machines, due to various causes, a person's renal system can fail. Renal failure produces several physiological derangements. It is no longer possible to balance water and minerals or to excrete daily metabolic load. Toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that normal functioning kidneys would otherwise remove. Dialysis treatment for replacement of kidney functions is critical to many people because the treatment is life saving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment (typically ten to ninety liters of such fluid). The substitution fluid and the fluid accumulated by the patient in between treatments is ultrafiltered over the course of the HF treatment, providing a convective transport mechanism that is particularly beneficial in removing middle and large molecules (in hemodialysis there is a small amount of waste removed along with the fluid gained between dialysis sessions, however, the solute drag from the removal of that ultrafiltrate is not enough to provide convective clearance).

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD (HF, HDF) treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that frequent treatments remove more toxins and waste products than a patient receiving less frequent but perhaps longer treatments. A patient receiving more frequent treatments does not experience as much of a down cycle as does an in-center patient, who has built-up two or three days' worth of toxins prior to a treatment. In certain areas, the closest dialysis center can be many miles from the patient's home causing door-to-door treatment time to consume a large portion of the day. HHD may take place overnight or during the day while the patient relaxes, works or is otherwise productive.

Another type of kidney failure therapy is peritoneal dialysis, which infuses a dialysis solution, also called dialysis fluid, into a patient's peritoneal cavity via a catheter. The dialysis fluid contacts the peritoneal membrane of the peritoneal cavity. Waste, toxins and excess water pass from the patient's bloodstream, through the peritoneal membrane and into the dialysis fluid due to diffusion and osmosis, i.e., an osmotic gradient occurs across the membrane. An osmotic agent in dialysis provides the osmotic gradient. The used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), and tidal flow dialysis and continuous flow peritoneal dialysis ("CFPD"). CAPD is a manual dialysis treatment. Here, the patient manually connects an implanted catheter to a drain to allow used or spent dialysate fluid to drain from the peritoneal cavity. The patient then connects the catheter to a bag of fresh dialysis fluid to infuse fresh dialysis fluid through the catheter and into the patient. The patient disconnects the catheter from the fresh dialysis fluid bag and allows the dialysis fluid to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to perform the treatment cycles manually and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal cavity. APD machines also allow for the dialysis fluid to dwell within the cavity and for the transfer of waste, toxins and excess water to take place. The source may include multiple sterile dialysis fluid bags.

APD machines pump used or spent dialysate from the peritoneal cavity, though the catheter, and to the drain. As with the manual process, several drain, fill and dwell cycles occur during dialysis. A "last fill" occurs at the end of APD and remains in the peritoneal cavity of the patient until the next treatment.

Any of the above modalities performed by a machine include components that wear out over time and need replacement. There is an inherent struggle to not replace components too often, leading to excess cost and repair time versus waiting for a complete component failure, after which the machine is down until the component is changed, leading to a disruption in a patient's treatment schedule, possible negative patient and doctor/clinician perception of the machine, and the need for servicing on an immediate basis.

U.S. Pat. No. 7,873,489, entitled, Dialysis Machine with Servicing Indicator", discloses one servicing regime. The regime looks basically at two factors, namely, time that the component has been installed versus duration of time used. The regime sets three limits including an upper limit for duration of time used, a lower limit for time that the component has been installed, and an upper limit for time that the component has been installed. A component is not eligible for replacement until it reaches its lower limit for time that the component has been installed, even if the upper limit for duration of time used has been met or exceeded. However, the component will be replaced when it reaches its upper limit for time that the component has been installed, regardless of its duration of time used.

While the servicing regime of U.S. Pat. No. 7,873,489 may be different than what was present in the prior art, it is believed that there is still substantial room for improvement.

SUMMARY

The servicing regime described herein is applicable, for example, to fluid delivery for: plasmapherisis, hemodialysis ("HD"), hemofiltration ("HF") hemodiafiltration ("HDF"), and continuous renal replacement therapy ("CRRT") treatments. The servicing regime described herein is also applicable to peritoneal dialysis ("PD") and to intravenous drug delivery. These modalities may be referred to herein collectively or generally individually as medical fluid delivery.

Moreover, the servicing regime described herein may be used with clinical or home-based machines. For example, the systems may be employed in in-center HD, HF or HDF machines, which run throughout the day. Alternatively, the systems may be used with home HD, HF or HDF machines, which are operated at the patient's convenience. One such home system is described in U.S. Pat. No. 8,029,454 ("the '454 Patent"), issued Oct. 4, 2011, entitled "High Convection Home Hemodialysis/Hemofiltration And Sorbent System", filed Nov. 4, 2004, assigned to the assignee of the present application. Other such home systems are described in U.S. Pat. No. 8,393,690 ("the '690 Patent"), issued Mar. 12, 2013, entitled "Enclosure for a Portable Hemodialysis System", filed Aug. 27, 2008. The entire contents of each of the above references are incorporated herein by reference and relied upon.

In an embodiment, a medical fluid delivery machine is provided that includes a medical fluid delivery chassis. The medical fluid delivery chassis houses components needed to deliver medical fluid, such as one or more pump, plural valves, a heater if needed, online medical fluid generation equipment if needed and desired, plural sensors, such as any one, or more, or all of pressure sensors, conductivity sensors, temperature sensors, air detectors, blood leak detectors, and the like, a user interface, and a control unit, which may employ one or more processor and memory to control the above-described equipment. The medical fluid delivery machine may also include one or more filter, such as a dialyzer or hemofilter for cleansing blood and/or an ultrafilter for purifying water, dialysis fluid, or other fluid.

Any of the operating components used in connection with the medical fluid delivery machine may be subject to the servicing regime of the present disclosure. Certain ones of the components, such as a pump actuator, valve actuator or heater, are built to last for a long time. Other components, such as a filter, are known to have a relatively short life compared with the long life components. Thus, each component of the machine may have its own service life expectancy or be classified into one of different categories of life expectancy. To a certain extent, the servicing regime of the present disclosure is more applicable to shorter life expectancy components and to longer life components nearing the end of their expected life. In any case, however, the servicing regime of the present disclosure may be applied to any operating component of the medical fluid delivery machine. "Operating component" may, but does not have to, mean a component of the medical fluid delivery machine, or a peripheral thereto, which generates operating data or data that may be tested to generate test data.

In one embodiment, the servicing regime analyzes self-test data over time to analyze a component. For example, assume that the machine provides an ultrafilter that purifies water, dialysis fluid or other fluid. The machine may then run a self-test on the ultrafilter before each treatment. The ultrafilter includes thin semi-permeable membranes, the walls of which have tiny pores that allow the liquid to pass and be filtered. If one of the membranes tears or if the pores begin to open, then the particulate that is intended to be filtered may pass through the tear or opened pores, such that the ultrafilter is not able to clean the liquid as well as it once could. One self-test is then to run a pressure decay test on the membranes prior to treatment to see how much the membranes leak.

It is contemplated in the regime of the present disclosure to set two limits for the pressure decay test, namely, a first replacement limit which if reached results in the ultrafilter having to be replaced. A second, soft, limit is also set, which tells the operator that this particular ultrafilter has begun to degrade and that it should be monitored more closely, so that the ultrafilter may be replaced when its leakage rate is close to but not at the replacement limit. There are multiple advantages of the soft limit warning. First, the machine has enjoyed most or even close to all of the useful life of the ultrafilter. Second, the replacement is made presumably at a convenient time for all parties involved and is done so on a "good idea" basis as opposed to a "must" basis. The machine is only down for the time needed to replace the component. The patient and clinician/doctor do not have to wait until a part arrives to run another treatment.

In another embodiment, the servicing regime analyzes component performance data over time, alternatively or additionally to the self-test data. As discussed above, one example self-test for an ultrafilter is a pressure decay test that looks for leaks. In addition to leaks, ultrafilters may need to be replaced if they become clogged. As mentioned above, properly working ultrafilter membranes trap particulate and allow purified liquid to pass. The trapped particulate forms a concentrated slurry with liquid that does not pass through the membranes. It is intended that the slurry be forced back to the inlet side of the ultrafilter or to drain. However, the particulate instead of traveling with the slurry may instead imbed itself into the walls of the membranes and begin to clog the ultrafilter.

It is accordingly contemplated to monitor the performance output of a component, such as the ultrafilter. For example, it is contemplated to monitor the flowrate downstream of the ultrafilter. Replacement and soft limits are set again for the flowrate monitoring. After the soft limit is reached, the output flowrate performance of ultrafilter is monitored closely. The ultrafilter may then be replaced slightly before reaching the replacement flowrate limit, thus extending ultrafilter life as much as possible, while still maintaining a relatively high performance level.

A single component, such as the ultrafilter example, may accordingly have multiple criteria by which they are judged under the servicing regime of the present disclosure. Each criterion has its own soft limit that is evaluated independently to determine when to change the component.

The criterion may be evaluated for reasons in addition to the possible replacement of a component. For example, data may be collected from multiple machines and evaluated to determine the most appropriate time to order or build new ones of the components. For example, the ultrafilter may be purchased from an outside company or be made in-house. But in either case, the component likely needs to be produced and ordered in a minimum quantity. If for example, the minimum order or production quantity for the ultrafilters is 100 pieces, there are only 20 ultrafilters left in stock, and there are 30 ultrafilters in the field that are at or below the soft limit, the system of the present disclosure may provide a prompt so that purchasing personnel may quickly place a new order for ultrafilters. In this manner, new components are ordered only when needed but in time so that there is no shortage of the component.

The servicing regime of the present disclosure may be implemented on a machine level, on an overarching platform system level that oversees many machines, or a combination of same. Continuing with the ultrafilter example, in one embodiment, each machine keeps track of the results of the pressure decay test, the downstream flowrate monitoring, the replacement limit, and the soft limit. If a soft limit is reached, a display device of the machine may display an audio, visual or audiovisual alert to the operator informing of the occurrence and/or provide a servicing screen sharing same. The alert or servicing screen may include a graph showing pressure decay data or downstream flowrate data in the days leading up to and including data from the day that triggered the soft limit. The machine may be programmed to enter a "watch mode" after the soft limit is reached, in which the graph is updated each time new data is generated, so that the user can see how the ultrafilter is trending. Perhaps the data hovers around the soft limit, so that the ultrafilter may still be used. Or perhaps the data trends down towards the replacement limit, indicating that the ultrafilter needs to be replaced soon.

The machine may also calculate, using a current slope of the data line from the graph, or a curve formed mathematically from multiple data points, when the line would, assuming the slope or curve does not change, intersect the replacement limit. Thus, along with the graph, the machine in the "watch mode" may display an estimated amount of days or treatments until replacement is mandatory. The machine updates the estimate accordingly if the slope changes.

The "watch mode" output, including the graph and the number of days or treatments until replacement, may be displayed additionally or alternatively at a remote computer, such as a clinician's computer and/or a service person's computer. As discussed in detail below, it is contemplated to connect the machine via one or more server to a remote clinician computer and/or a service person's computer. After each treatment, the machine sends data via the one or more server to a database accessible by the clinician computer and/or the service person's computer. The "watch mode" data from multiple machines may be put into flagged folder. A service person, for example, may be tasked with routinely accessing the flagged folder to view "watch mode" data for multiple machines. The service person can then make a decision for each "watch mode" scenario whether or not to schedule a component replacement.

It is contemplated to provide the medical fluid delivery machines of the present disclosure to multiple clinics and to include each of the clinics under the overall system of the present disclosure. The service person, on the other hand, will typically support the manufacturer of the machines. The system is customizable then to enable each clinic to decide whether the clinic is to maintain its own machines or to instead contract the manufacturer's service personnel to maintain the machines. If the clinic maintains its own machines, the clinic may decide to let the machines themselves display the "watch mode" as described herein. Alternatively, the clinic may access the flag files over the server(s) to analyze the "watch mode" data. If the clinic decides to contract the manufacturer's service personnel to maintain the machines, the manufacturer's service personnel monitor the flag files remotely over the server(s) to access the "watch mode" data.

The example of the ultrafilter is used throughout this specification because it is a component that clearly benefits from the servicing regime of the present disclosure. Ultrafilters are known to have limited lives and are relatively expensive components. It is therefore desirable to obtain as much usage out of them as possible before replacement. The dialyzer and hemofilter are other good examples. Dialyzers and hemofilters may be sterilized and packaged as part of a complete blood set, which has to be replaced when the dialyzer leaks or deteriorates (clogs as is the case with the ultrafilter).

It should be appreciated that any component subjected to leak testing, such as pressure decay testing, may benefit from the servicing regime of the present disclosure. For instance, a treatment fluid pathway or blood flow pathway, or parts thereof, may be pressure checked and placed in a "watch mode" or replaced if needed. Fluid valves and pumps may be pressure checked and placed in a "watch mode" or replaced if needed. The fluid pumps may also be evaluated for downstream flowrate output. If the machine is driven pneumatically, its pneumatic solenoid valves may also be pressure checked and placed in a "watch mode" or replaced if needed.

It should also be appreciated that any sensing component whose output is capable of being tested, e.g., by subjecting to a known pressure, temperature, or conductivity sample, may benefit from the servicing regime of the present disclosure. Other suitable components are described herein.

In light of the disclosure herein and without limiting the disclosure in any way, in a first aspect of the present disclosure, which may be combined with any other aspect listed herein unless specified otherwise, a medical fluid delivery system includes: a medical fluid delivery machine including at least one component producing associated output data; at least one component replacement limit for the at least one component; and a computer programmed to store the at least one component replacement limit and to analyze the output data to provide an indication of how well the at least one component is performing relative to its component replacement limit.

In a second aspect of the present disclosure, which may be combined with any other aspect listed herein unless specified otherwise, the medical fluid delivery machine includes a display device, the computer provided by a control unit of the medical fluid delivery machine, and wherein the indication is displayed by the display device of the medical fluid delivery machine.

In a third aspect of the present disclosure, which may be combined with any other aspect listed herein unless specified otherwise, the computer is a remote computer having a display device, the medical fluid delivery machine in data communication with the remote computer via at least one server, and wherein the indication is displayed by the display device of the remote computer.

In a fourth aspect of the present disclosure, which may be combined with any other aspect listed herein unless specified otherwise, the associated output data includes a flowrate, and wherein at least one of the component replacement limits is a component replacement flowrate.

In a fifth aspect of the present disclosure, which may be combined with the fourth aspect in combination with any other aspect listed herein unless specified otherwise, the at least one component includes (i) a filter, the flowrate being a flowrate downstream of the filter, (ii) a medical fluid delivery pump, the flowrate being a flowrate downstream of the medical fluid delivery pump, or (iii) a disposable item, the flowrate being a flowrate downstream of the disposable item.

In a sixth aspect of the present disclosure, which may be combined with any other aspect listed herein unless specified otherwise, the system includes at least one component soft limit in addition to the at least one component replacement limit stored by the computer, and wherein the indication of how well the at least one component is performing relative to its component replacement limit includes whether the component is performing between its soft limit and its component replacement limit.

In a seventh aspect of the present disclosure, which may be combined with the sixth aspect in combination with any other aspect listed herein unless specified otherwise, the computer is programmed to generate at least one component performance graph showing the at least one component performing relative to its soft limit and its component replacement limit.

In an eighth aspect of the present disclosure, which may be combined with the sixth aspect in combination with any other aspect listed herein unless specified otherwise, the computer is programmed to generate an estimate of when component performance will reach its replacement limit when the at least one component is performing between its soft limit and its component replacement limit.

In a ninth aspect of the present disclosure, which may be combined with the sixth aspect in combination with any other aspect listed herein unless specified otherwise, the computer is a remote computer, the medical fluid delivery machine in data communication with the remote computer via at least one server, and which includes a file provided by the computer indicating each component performing between its soft limit and its component replacement limit.

In a tenth aspect of the present disclosure, which may be combined with the sixth aspect in combination with any other aspect listed herein unless specified otherwise, the computer is a remote computer, the medical fluid delivery machine in data communication with the remote computer via at least one server, and which includes a file provided by the computer indicating each component of each machine performing between its soft limit and its component replacement limit.

In an eleventh aspect of the present disclosure, which may be combined with any other aspect listed herein unless specified otherwise, the computer receives the output data associated with the component after each treatment performed by the medical fluid delivery device.

In a twelfth aspect of the present disclosure, which may be combined with any other aspect listed herein unless specified otherwise, a medical fluid delivery system includes: a medical fluid delivery machine including at least one component subjected to a test to produce test data; at least one component replacement limit for the at least one component; and a computer programmed to store the at least one component replacement limit and to analyze the test data to provide an indication of how well the at least one component is testing relative to its component replacement limit.

In a thirteenth aspect of the present disclosure, which may be combined with any other aspect listed herein unless specified otherwise, the at least one component includes a sensor for the medical fluid delivery machine, the test analyzing an output from the sensor.

In a fourteenth aspect of the present disclosure, which may be combined with the thirteenth aspect in combination with any other aspect listed herein unless specified otherwise, the sensor is a pressure sensor, conductivity sensor or a temperature sensor.

In a fifteenth aspect of the present disclosure, which may be combined with any other aspect listed herein unless specified otherwise, the medical fluid delivery machine includes an air pressure source, a pressure sensor, and wherein the test is a pressure decay test in which the at least one component is subjected to air pressure via the source, which is sensed by the pressure sensor.

In a sixteenth aspect of the present disclosure, which may be combined with the fifteenth aspect in combination with any other aspect listed herein unless specified otherwise, the at least one component includes (i) a filter including a filtering membrane, the pressure decay test testing the filtering membrane, (ii) a fluid delivery component, the pressure decay test testing the fluid delivery component for a leak, (iii) a disposable component, the pressure decay test testing the disposable component for a leak or (iv) a fluid line, the pressure decay test testing the fluid line for a leak.

In a seventeenth aspect of the present disclosure, which may be combined with any other aspect listed herein unless specified otherwise, the medical fluid delivery machine includes a display device, the computer provided by a control unit of the medical fluid delivery machine, and wherein the indication is displayed by the display device of the medical fluid delivery machine.

In an eighteenth aspect of the present disclosure, which may be combined with any other aspect listed herein unless specified otherwise, the computer is a remote computer having a display device, the medical fluid delivery machine in data communication with the remote computer via at least one server, and wherein the indication is displayed by the display device of the remote computer.

In a nineteenth aspect of the present disclosure, which may be combined with any other aspect listed herein unless specified otherwise, the system includes at least one component soft limit in addition to the at least one component replacement limit stored by the computer, and wherein the indication of how well the at least one component is testing relative to its component replacement limit includes whether component testing performance is between its soft limit and its component replacement limit.

In a twentieth aspect of the present disclosure, which may be combined with the nineteenth aspect in combination with any other aspect listed herein unless specified otherwise, the computer is programmed to generate at least one testing performance graph showing the at least one component testing performance relative to its soft limit and its component replacement limit.

In a twenty-first aspect of the present disclosure, which may be combined with the nineteenth aspect in combination with any other aspect listed herein unless specified otherwise, the computer is programmed to generate an estimate of when component testing performance will reach its replacement limit when the at least one component testing performance is between its soft limit and its component replacement limit.

In a twenty-third aspect of the present disclosure, which may be combined with the nineteenth aspect in combination with any other aspect listed herein unless specified otherwise, the computer is a remote computer, the medical fluid delivery machine in data communication with the remote computer via at least one server, and which includes a file provided by the computer indicating each component having testing performance between its soft limit and its component replacement limit.

In a twenty-fourth aspect of the present disclosure, which may be combined with the nineteenth aspect in combination with any other aspect listed herein unless specified otherwise, the computer is a remote computer, the medical fluid delivery machine in data communication with the remote computer via at least one server, and which includes a file provided by the computer indicating each component of each machine having testing performance between its soft limit and its component replacement limit.

In a twenty-fifth aspect of the present disclosure, which may be combined with any other aspect listed herein unless specified otherwise, the computer receives the test data associated with the component after each treatment performed by the medical fluid delivery device.

In a twenty-sixth aspect of the present disclosure, which may be combined with any other aspect listed herein unless specified otherwise, a medical fluid delivery system includes: a medical fluid delivery machine including at least one component yielding associated output data and associated test data; at least one component output replacement limit for the at least one component; at least one component testing replacement limit for the at least one component; and a computer programmed to store the at least one component output replacement limit and the at least one component testing replacement limit and to analyze the output data and the test data to provide a first indication of how well the at least one component is performing relative to its component output replacement limit and a second indication of how well the at least one component is testing relative its the component testing replacement limit.

In a twenty-seventh aspect of the present disclosure, which may be combined with any other aspect listed herein unless specified otherwise, a medical fluid delivery system includes: a medical fluid delivery machine including a component yielding at least one of associated output data or associated test data; at least one of a (i) component output replacement limit and a component output soft limit for the component or (ii) a component testing replacement limit or a component testing soft limit for the component; and a computer programmed to store at least one of (i) or (ii), and for (i) analyze the output data to provide a first indication of how well the component is performing relative to the component output replacement limit and the component output soft limit, and for (ii) analyze the test data to provide a second indication of how well the at least one component is testing relative to the component testing replacement limit and the component testing soft limit.

In a twenty-eighth aspect of the present disclosure, which may be combined with any other aspect listed herein unless specified otherwise, a medical fluid delivery system includes: a medical fluid delivery machine operating with a disposable set over multiple treatments to mix for each treatment at least one concentrate with water made suitable for a desired medical fluid treatment to form a medical fluid; a sensor configured to test the accuracy of the medical fluid mixed by the medical fluid delivery machine, the sensor producing an output enabling mixing accuracy to be determined; and a computer programmed to determine mixing accuracies from the mixing accuracy outputs produced by the sensor and determine whether the disposable set needs to be replaced.

In a twenty-ninth aspect of the present disclosure, which may be combined with the twenty-eighth aspect in combination with any other aspect listed herein unless specified otherwise, the computer is programmed to use a rolling average to determine whether the disposable set needs to be replaced.

In a thirtieth aspect of the present disclosure, which may be combined with the twenty-eighth aspect in combination with any other aspect listed herein unless specified otherwise, the computer is a computer for the medical fluid delivery machine or a computer located remote from the medical fluid delivery machine.

In a thirty-first aspect of the present disclosure, which may be combined with the twenty-eighth aspect in combination with any other aspect listed herein unless specified otherwise, the computer is programmed to determine at least one of whether the disposable set needs to be replaced (i) now or (ii) for a treatment in the future.

In a thirty-second aspect of the present disclosure, any of the structure and functionality disclosed in connection with FIGS. 1 to 8 may be combined with any of the other structure and functionality disclosed in connection with FIGS. 1 to 8.

In light of the present disclosure and the above aspects, it is therefore an advantage of the present disclosure to provide an improved medical fluid delivery device.

It is another advantage of the present disclosure to provide an improved servicing regime for medical fluid delivery devices.

It is a further advantage of the present disclosure to efficiently replace medical fluid delivery machine components.

It is still another advantage of the present disclosure to help prevent downtime due to having to wait for a component replacement.

It is still a further advantage of the present disclosure to provide an efficient way for ordering and stocking medical fluid delivery machine components.

It is yet another advantage of the present disclosure to provide a system that is flexible to the servicing needs of different medical fluid delivery machine users.

It is yet a further advantage of the present disclosure to provide a servicing regime that is applicable to different types of components used in a medical fluid delivery machine.

The advantages discussed herein may be found in one, or some, and perhaps not all of the embodiments disclosed herein. Additional features and advantages are described herein, and will be apparent from, the following Detailed Description and the figures.

BRIEF DESCRIPTION OF THE FIGURES

FIG. 6 illustrates a watch mode screen for a single machine showing which of its components have output metrics at or below a soft limit of the present disclosure.

FIG. 7 illustrates a flag or watch mode screen for multiple machines showing which machines have at least one component with output metrics at or below a soft limit of the present disclosure.

DETAILED DESCRIPTION

The examples described herein are applicable to any medical fluid delivery system that delivers a medical fluid, such as blood, dialysis fluid, substitution fluid or and intravenous drug ("IV"). The examples are particularly well suited for kidney failure therapies, such as all forms of hemodialysis ("HD"), hemofiltration ("HF"), hemodiafiltration ("HDF"), continuous renal replacement therapies ("CRRT") and peritoneal dialysis ("PD"), referred to herein collectively or generally individually as renal failure therapy. Moreover, the machines and the servicing regimes described herein may be used in clinical or home settings. For example, a machine operating with the servicing regime of the present disclosure may be employed in an in-center HD machine, which runs virtually continuously throughout the day. Alternatively, the servicing regime of the present disclosure may be used in a home HD machine, which can for example be run at night while the patient is sleeping.

Figure 1:
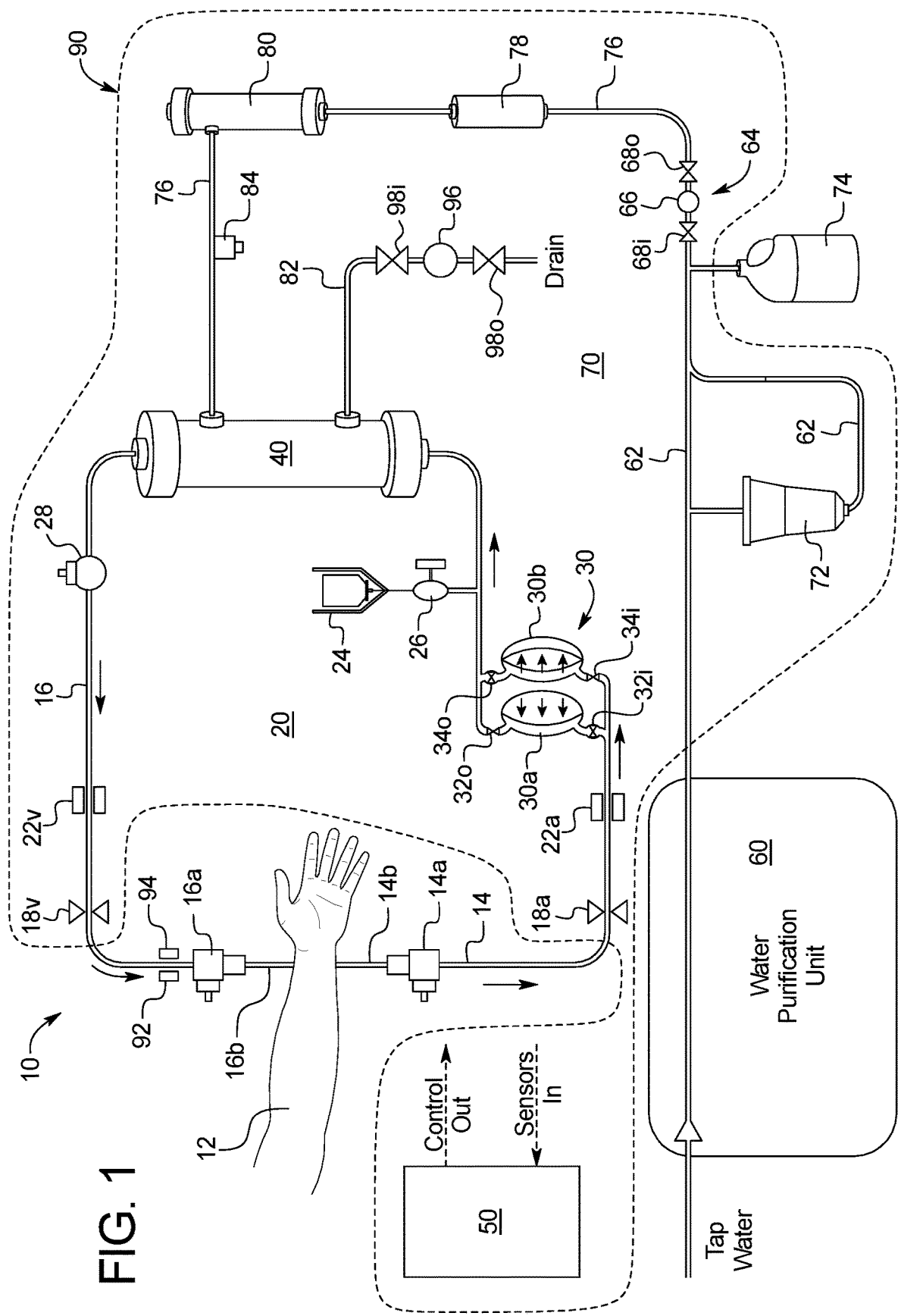
FIG. 1 is a schematic illustration of one embodiment of a medical fluid delivery machine of the present disclosure.

Referring now to FIG. 1, an example of an HD flow schematic for a medical fluid delivery system 10 operating with the servicing regime of the present disclosure is illustrated. Because the HD system of FIG. 1 is relatively complicated, FIG. 1 and its discussion also provide support for any of the renal failure therapy modalities discussed above and for an IV or drug delivery machine. Generally, system 10 is shown having a very simplified version of a dialysis fluid or process fluid delivery circuit. The blood circuit is also simplified but not to the degree that the dialysis fluid circuit is simplified. It should be appreciated that the circuits have been simplified to make the description of the present disclosure easier, and that the systems if implemented would have additional structure and functionality, such as is found in the publications incorporated by reference above.

System 10 of FIG. 1 includes a blood circuit 20. Blood circuit 20 pulls blood from and returns blood to a patient 12. Blood is pulled from patient 12 via an arterial line 14, and is returned to the patient via a venous line 16. Arterial line 14 includes an arterial line connector 14a that connects to an arterial needle 14b, which is in blood draw communication with patient 12. Venous line 16 includes a venous line connector 16a that connects to a venous needle 16b, which is in blood return communication with the patient. Arterial and venous lines 14 and 16 also include line clamps 18a and 18v, which can be spring-loaded, fail-safe mechanical pinch clamps. Line clamps 18a and 18v are closed automatically in an emergency situation in one embodiment.

Arterial and venous lines 14 and 16 also include air or bubble detectors 22a and 22v, respectively, which can be ultrasonic air detectors. Air or bubble detectors 22a and 22v look for air in the arterial and venous lines 14 and 16, respectively. If air is detected by one of air detectors 22a and 22v, system 10 closes line clamps 18a and 18v, pauses the blood and dialysis fluid pumps, and provides instructions to the patient to clear the air so that treatment can resume.

A blood pump 30 is located in arterial line 14 in the illustrated embodiment. In the illustrated embodiment, blood pump 30 includes a first blood pump pod 30a and a second blood pump pod 30b. Blood pump pod 30a operates with an inlet valve 32i and an outlet valve 32o. Blood pump pod 30b operates with an inlet valve 34i and an outlet valve 34o. In an embodiment, blood pump pods 30a and 30b are each blood receptacles that include a hard outer shell, e.g., spherical, with a flexible diaphragm located within the shell, forming a diaphragm pump. One side of each diaphragm receives blood, while the other side of each diaphragm is operated by negative and positive air pressure. Blood pump 30 is alternatively a peristaltic pump operating with the arterial line 14 tube.

A heparin vial 24 and heparin pump 26 are located between blood pump 30 and blood filter 40 (e.g., dialyzer) in the illustrated embodiment. Heparin pump 26 may be a pneumatic pump or a syringe pump (e.g., stepper motor driven syringe pump). Supplying heparin upstream of blood filter 40 helps to prevent clotting of the filter's membranes.

A primary control processor ("ACPU") or control unit 50 includes one or more processor and memory. Control unit 50 receives air detection signals from air detectors 22a and 22v (and other sensors of system 10, such as temperature sensors, blood leak detectors, conductivity sensors, pressure sensors, and access disconnection transducers 102, 104), and controls components such as line clamps 18a and 18v, blood pump 30, heparin pump 26, and the dialysis fluid pumps. Blood exiting blood filter 40 via venous line 16 flows through an airtrap 28. Airtrap 28 removes air from the blood before the dialyzed blood is returned to patient 12 via venous line 16.

With the hemodialysis version of system 10 of FIG. 1, dialysis fluid or dialysate is pumped along the outside of the membranes of blood filter 40, while blood is pumped through the insides of the blood filter membranes. Dialysis fluid or dialysate is prepared beginning with the purification of water via a water purification unit 60. One suitable water purification unit is set forth in U.S. Patent Publication No. 2011/0197971, entitled, "Water Purification System and Method", filed Apr. 25, 2011, the entire contents of which are incorporated herein by reference and relied upon. In one embodiment, water purification unit includes filters and other structures to purify tap water (e.g., remove pathogens and ions such as chlorine), so that the water is in one implementation below 0.03 endotoxin units/ml ("EU/ml") and below 0.1 colony forming units/ml ("CFU/ml"). Water purification unit 60 may be provided in a housing separate from the housing or chassis of the hemodialysis machine, which includes blood circuit 20 and a dialysis fluid circuit 70.

Dialysis fluid circuit 70 is again highly simplified in FIG. 1 to ease illustration. Dialysis fluid circuit 70 in actuality may include all of the relevant structure and functionality set forth in the publications incorporated by reference above. Certain features of dialysis fluid circuit 70 are illustrated in FIG. 1. In the illustrated embodiment, dialysis fluid circuit 70 includes a to-blood filter dialysis fluid pump 64. Pump 64 is in one embodiment configured the same as blood pump

30. Pump 64, like pump 30, includes a pair of pump pods 66 each having inlet valves 68i and outlet valves 68o, which again may be spherically configured. The two pump pods, like with blood pump 30, are operated alternatingly so that one pump pod is filling with HD dialysis fluid, while the other pump pod is expelling HD dialysis fluid.

Pump 64 is a to-blood filter dialysis fluid pump. There is another dual pod pump chamber 96 operating with valves 98i and 98o located in drain line 82 to push used dialysis fluid to drain. There is a third pod pump (not illustrated) for pumping pump purified water through a bicarbonate cartridge 72. There is a fourth pod pump (not illustrated) used to pump acid from acid container 74 into mixing line 62. The third and fourth pumps, the concentrate pumps, may be single pod pumps because continuous pumping is not as important in mixing line 62 due to a buffering dialysis fluid tank (not illustrated) between mixing line 62 and to-blood filter dialysis fluid pump 64 in one embodiment.

A fifth pod pump (not illustrated) provided in drain line 82 is used to remove a known amount of ultrafiltration ("UF") when an HD therapy is provided. System 10 keeps track of the UF pump to control and know how much ultrafiltrate has been removed from the patient. System 10 ensures that the necessary amount of ultrafiltrate is removed from the patient by the end of treatment.

Each of the above-described pumps may alternatively be a peristaltic pump operating with a pumping tube. If so, the system valves may still be actuated pneumatically according to the features of the present disclosure.

In one embodiment, purified water from water purification unit 60 is pumped along mixing line 62 though bicarbonate cartridge 72. Acid from container 74 is pumped along mixing line 62 into the bicarbonated water flowing from bicarbonate cartridge 72 to form an electrolytically and physiologically compatible dialysis fluid solution. The pumps and temperature-compensated conductivity sensors used to properly mix the purified water with the bicarbonate and acid are not illustrated but are disclosed in detail in the publications incorporated by reference above.

FIG. 1 also illustrates that dialysis fluid is pumped along a fresh dialysis fluid line 76, through a heater 78 and an ultrafilter 80, before reaching blood filter 40, after which used dialysis fluid is pumped to drain via drain line 82. Heater 78 heats the dialysis fluid to body temperature or about 37° C. Ultrafilter 80 further cleans and purifies the dialysis fluid before reaching blood filter 40, filtering bugs or contaminants introduced for example via bicarbonate cartridge 72 or acid container 74 from the dialysis fluid.

Dialysis fluid circuit 70 also includes a sample port 84 in the illustrated embodiment. Dialysis fluid circuit 70 will further include a blood leak detector (not illustrated but used to detect if a blood filter 40 fiber is torn) and other components that are not illustrated, such as balance chambers, plural dialysis fluid valves, and a dialysis fluid holding tank, all illustrated and described in detail in the publications incorporated by reference above.

In the illustrated embodiment, hemodialysis system 10 is an online, pass-through system that pumps dialysis fluid through blood filter one time and then pumps the used dialysis fluid to drain. Both blood circuit 20 and dialysis fluid circuit 70 may be hot water disinfected after each treatment, such that blood circuit 20 and dialysis fluid circuit 70 may be reused. In one implementation, blood circuit 20 including blood filter 40 is hot water disinfected and reused daily for about one month, while dialysis fluid circuit 70 is hot water disinfected and reused for about six months.

In alternative embodiments, for CRRT for example, multiple bags of sterilized dialysis fluid or infusate are ganged together and used one after another. In such a case, the emptied supply bags can serve as drain or spent fluid bags.

The machine 90 of system 10 includes an enclosure as indicated by the dashed line of FIG. 1. The enclosure of machine 90 varies depending upon the type of treatment, whether the treatment is in-center or a home treatment, and whether the dialysis fluid/infusate supply is a batch-type (e.g., bagged) or on-line.

Figure 2:
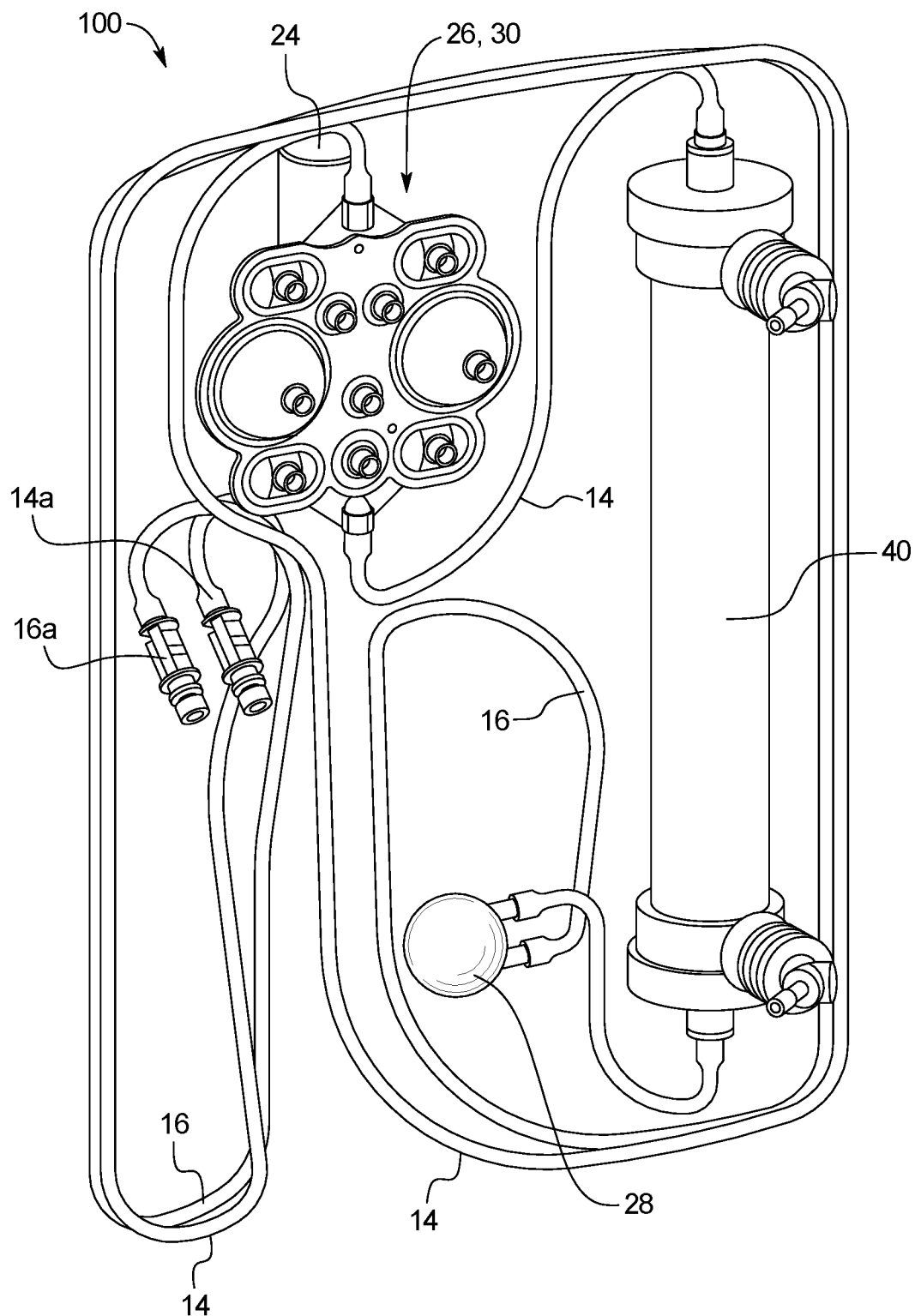
FIG. 2 is a perspective view illustrating a blood set for use with one embodiment of the medical fluid delivery machine of FIG. 1.

FIG. 2 illustrates that machine 90 of system 10 of FIG. 1 may operate with a blood set 100. Blood set 100 includes arterial line 14, venous line 16, heparin vial 24, heparin pump 26/blood pump 30 and blood filter 40 (e.g., dialyzer). An airtrap 28 may be located in venous line 16 to remove air from the blood before being returned to patient 12. Air detectors 22a and 22v contact arterial and venous lines 14 and 16, respectively, for operation.

In FIGS. 1 and 2, any of pumps 26, 30 (30a and 30b), 64, 96 (and other pumps not illustrated) and any of the valves, such as valves 32i, 32o, 34i, 34o, 68i, 68o, 98i, and 98o may be pneumatically actuated. In an embodiment, each of the pumps and valves has a fluid side and an air side, separated by a flexible membrane. Negative pneumatic pressure may be applied to the air side of the membrane to draw fluid into a pump chamber or to open a valve (or the pump or valve could be opened by venting positive closing pressure to atmosphere and allowing fluid pressure to open). Positive pneumatic pressure is applied to the air side of the membrane to expel fluid from a pump chamber or to close a valve.

Figure 3:
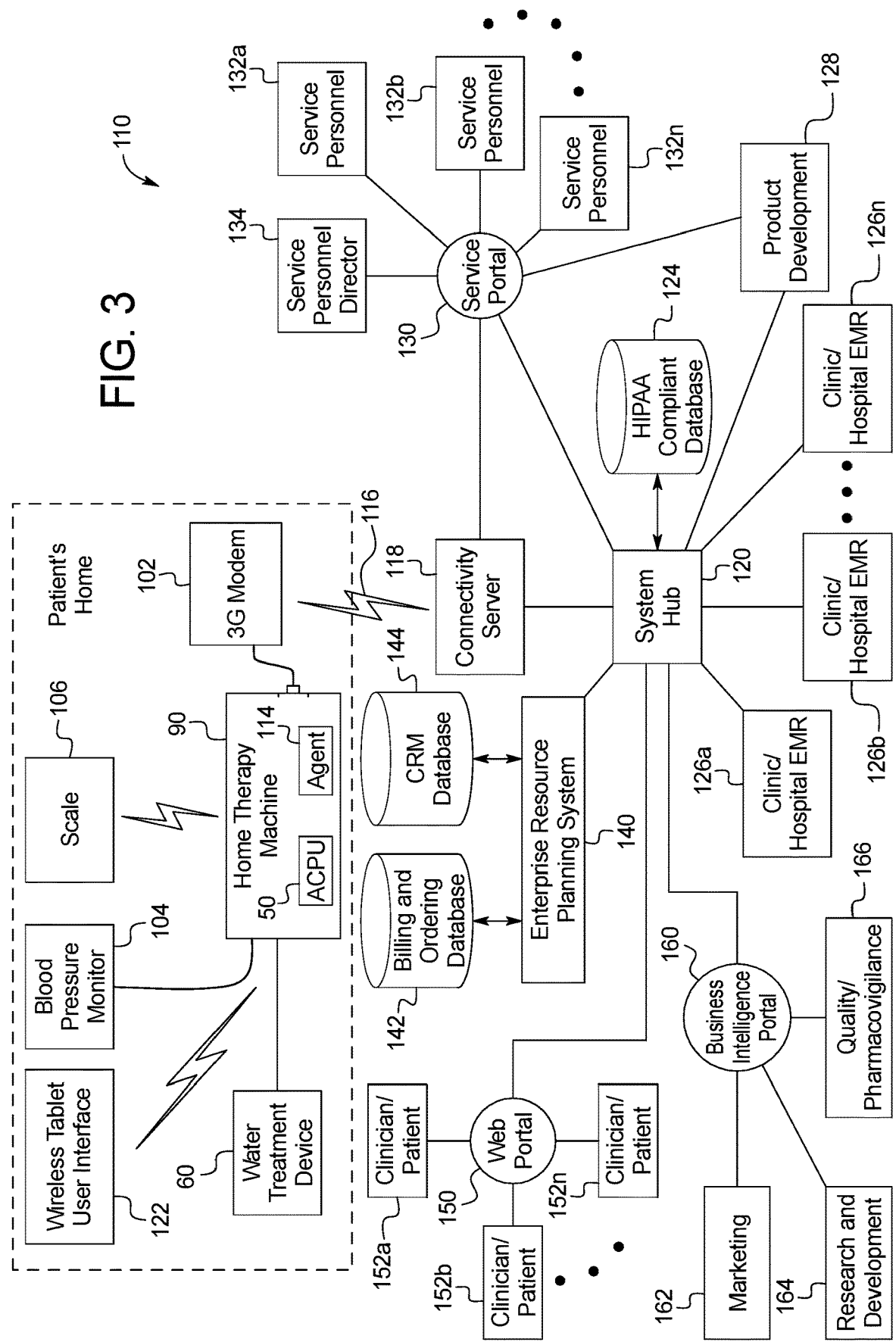
FIG. 3 is a schematic view illustrating one embodiment for a system that incorporates the medical fluid delivery machines of the present disclosure, so that data may be obtained from such machines.

Referring now to FIG. 3, system 10 is illustrated operating within a larger platform system 110. System 110 incorporates many medical fluid delivery machines 90 and thus many associated medical fluid delivery machine systems 10. Machines 90 of platform system 110 may be of a same type (e.g., all HD machines) or be of different types (e.g., a mix of HD, PD, CRRT, medical delivery).

While a single medical fluid delivery machine 90 is illustrated as communicating with a connectivity server 118, system 110 oversees the operation of a plurality of medical fluid delivery machines, of the same type or of different types listed above. For example, there may be M number of hemodialysis machines 90, N number of hemofiltration machines 90, O number of CRRT machines 90, P number of peritoneal dialysis machines 90, Q number of home drug delivery machines 90, and R number of nutritional home therapy machines 90 connected to server 118 and operating with system 110. The numbers M through R may be the same or different numbers, and may be zero, one, or more than one. In FIG. 3, medical fluid delivery machine 90 is illustrated as a home therapy machine 90. However, as discussed below, medical fluid delivery machine 90 does not have to be used at home (indicated by dashed lines) and may instead be used in a hospital or clinic.

Home therapy machine 90 may receive at its front end purified water from a water treatment device 60 as discussed above. Water treatment device 60 connects to home therapy machine 90 via an Ethernet cable in an embodiment. Home therapy machines 90 of system 110 in the illustrated embodiment operate with other devices besides water treatment device 60, such as a blood pressure monitor 104, a weigh scale, e.g., wireless weigh scale 106, and a user interface such as a wireless tablet user interface 122. Home therapy machine 90 connects to server 118 wirelessly in one embodiment via a modem 102. Each of these components may (but does not have to be) located within the patient's home, as demarcated by the dashed lines in FIG. 3. Any one, or more or all of components 60, 104, 106 and 122 may communicate wired or wirelessly with home therapy machine 90. Wireless communication may be via Bluetooth™ WiFi™ Zigbee®, Z-Wave®, wireless Universal Serial Bus ("USB"), infrared, or any other suitable wireless communication technology. Alternatively, any one, or more or all of components 60, 104, 106 and 122 may communicate with home therapy machine 90 via wired communication.

Connectivity server 118 communicates with much of home medical device system 110 via a home medical device system hub 120. System hub 120 enables data and information concerning each home therapy machine 90 and its peripherals to travel back and forth via connectivity server 118 between machines 90 and the other clients connected to server 118. In the illustrated embodiment, system hub 120 is connected to a service portal 130, an enterprise resource planning system 140, a web portal 150, a business intelligence portal 160, a HIPAA compliant database 124, a product development team 128 and electronic medical records databases 126a to 126n.

Electronic medical records ("EMR") databases 126a to 126n store electronic information concerning patients. System hub 120 may send the data collected from log files of machine 90 to hospital or clinic databases 126a to 126n to merge or supplement that patient's medical records. Databases 126a to 126n may contain patient-specific treatment and prescription data and therefore access to such databases may be highly restricted. Enterprise resource planning system 140 obtains and compiles data generated via the patient and clinician website access, such as complaints, billing information and life cycle management information. Web portal 150 enables patients and clinics 152a to 152n treating the patients to access a website publicly available for users of system 110. Business intelligence portal 160 collects data from system hub 120 and provides data to marketing 162, research and development 164, and quality/pharmacovigilance 166.

It should be appreciated that the systems, methods and procedures described herein may be implemented using one or more computer programs or components. The programs of components may be provided as a series of computer instructions on any conventional computer-readable medium, including random access memory ("RAM"), read only memory ("ROM"), flash memory, magnetic or optical disks, optical memory, or other storage media. The instructions may be configured to be executed by a processor, which when executing the series of computer instructions performs or facilitates the performance of all or part of the disclosed methods and procedures.

In one embodiment, home therapy machine 90 performs a home treatment, such as home hemodialysis on a patient at the patient's home and then reports the results of that treatment to clinicians, doctors and nurses who are responsible for managing the health and well-being of that patient. The results of the treatment may include data from therapy machine and data from its peripherals including water treatment device 60. Water treatment device 60 data may include, for example, total volume of water delivered, quality of water delivered (e.g., chlorine content), how many different times water treatment device 60 delivered water to therapy machine 90 over the course of a treatment (this data could be monitored by device 60 or machine 90), average flowrate of the water delivered, any alarms or alerts that water treatment device 60 experienced over a treatment, and/or an amount of time or number of cycles performed over the course of a treatment, e.g., for component replacement information.

Home therapy machines 90 in an embodiment write log files using, e.g., a Linux™ operating system. The log files document pertinent home therapy machine 90 data, including peripheral device data. The log files may include any one or more of Extensible Markup Language ("XML"), comma-separated values ("CSV") or text files. The log files are placed into a file server box of the software of home therapy machine 90. It is also contemplated to store data at a peripheral device, e.g., water treatment device 60, which is not sent to machine 90. Such data may otherwise be obtained via the wired or wireless connection to the peripheral device or downloaded through other data connections or storage media. For example, a service person can access additional data via a laptop connected to water treatment device 60 or wireless weigh scale 106, e.g., via an Ethernet connection. Or, the additional data may be retrieved remotely from the peripheral devices, with home therapy machine 90 serving as the data transfer liaison between the peripheral device and authorized clients of system 110.

In one embodiment, home therapy machine 90, e.g., via the Internet, uses a connectivity service to transfer data between modem 102 and system hub 120. Here, a dedicated line may be provided at each patient's home for connecting the home therapy machine 90 to the connectivity server 118 via modem 102. Home therapy machine 90 in one embodiment accesses the Internet using a separate, e.g., 3G, 4G or 5G, modem 102. Modem 102 may use an Internet Service Provider ("ISP"), such as Vodafone™. In one implementation, a connectivity agent 114 developed by a connectivity service provider (e.g., provider of connectivity server 118) is installed onto the home therapy machine 90 and run on ACPU 50 of the machine. One suitable connectivity service is provided by Axeda™, which provides a secure managed connection 116 between medical devices and the connectivity server 118.

Connectivity agent 114 allows the home therapy machine 90 to connect to connectivity server 118 and transfer data to and from the connectivity server 118. The connectivity service operating via agent 114 and server 118 ensures that the connection with machine 90 is secure, ensures that the data correctly passes through machine 90's firewalls, checks whether there has been a data or system crash, and ensures that connectivity server 118 is communicating with the correct home therapy machine 90.

In one embodiment, home therapy machine 90 may only connect to connectivity server 118 when connectivity agent 114 is turned on or activated. During treatment and post-treatment disinfection, while machine 90 and its peripherals are functioning, connectivity agent 114 is turned off if one embodiment, which prevents home therapy machine 90 from communicating with any entity and sending or receiving data during treatment and disinfection or when machine 90 is live or running. When home therapy machine 90 is idle, e.g., after treatment and post-disinfection is complete, ACPU 112 turns connectivity agent 114 on in one embodiment. In an embodiment, connectivity agent 114 is off only during treatment (including pretreatment). After treatment, connectivity agent 114 retrieves the log files from the home therapy machine 90 and transfers data to the connectivity server 118 using the connectivity service. The connectivity service routes data packets to their proper destination but in one embodiment does not modify, access, or encrypt the data.

In system 110 of FIG. 3, the connectivity service via connectivity server 118 may communicate data to various places via a system hub 120, such as a service portal 130, clinics or hospitals 126a to 126n, and a web portal 150. Connectivity server 118 allows service personnel 132a to 132n and/or clinicians to track and retrieve various assets across the network, such as appropriate home therapy machines 90 and 3G, 4G or 5G modem 102, and their associated information, including machine or modem serial numbers. Connectivity server 118 may also be used to receive and provide firmware upgrades, approved by a director of service personnel 134 and obtained remotely via service portal 130, to authorized home therapy machines 90 and associated peripherals, such as water treatment devices 60.

The servicing regimes described herein may be performed in multiple places when viewing FIG. 3. When the medical fluid delivery machines 90 are home therapy machines, the servicing regimes or the present disclosure may be provided at the computers of service personnel 132a to 132n or at the computers of doctors or clinicians 126a to 126n. A patient at home is generally associated with a hospital or clinic 126a to 126n. That hospital or clinic may decide to service its own machines, in which case the servicing regimes of the present disclosure are provided at the computers of doctors or clinicians 126a to 126n. Or, that hospital or clinic may decide to have the machine manufacturer associated with overall system 110 service the machines, in which case the servicing regimes of the present disclosure are provided at the computers of service personnel 132a to 132n (but may still be viewable at the computers of doctors or clinicians 126a to 126n).

In another embodiment, medical fluid delivery machines 90 are not provided in the patient's home but are instead provided in hospitals or clinics 126a to 126n. Here, the hospital or clinic has three choices, namely, (i) the hospital or clinic contracts machine manufacturer associated with overall system 110 to service the machines, such that the servicing regimes of the present disclosure are provided at the computers of service personnel 132a to 132, (ii) hospital or clinic services its own machines and provides the servicing regimes of the present disclosure at the computers of doctors or clinicians 126a to 126n, or (iii) hospital or clinic services its own machines and provides the servicing regimes of the present disclosure at machines 90 themselves. In option (iii), machines 90 may, but do not have to, have the networking described herein, e.g., using connectivity server 118 or system hub 120.

Figure 4:
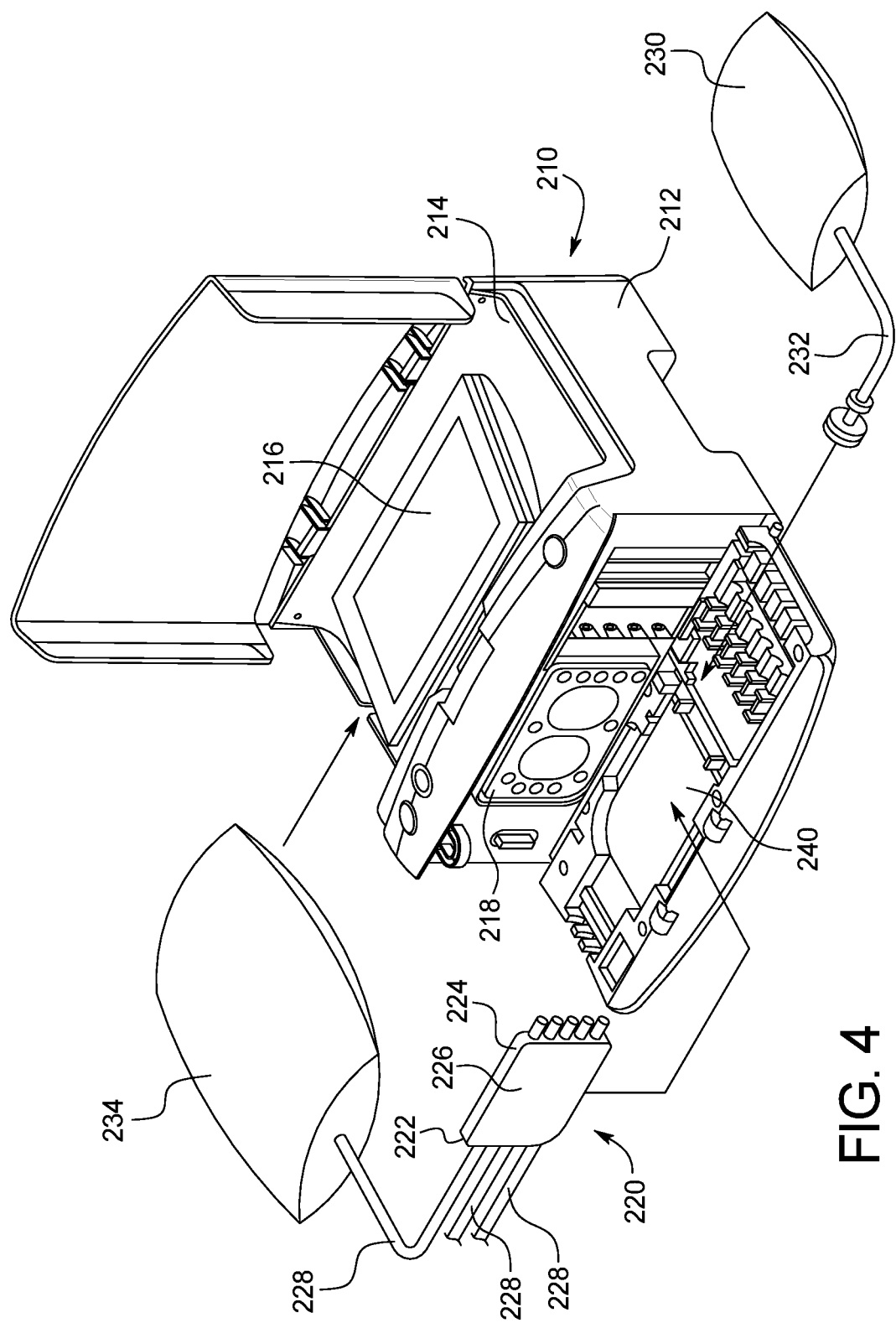
FIG. 4 is a perspective view of one embodiment of a peritoneal dialysis system including a cycler and disposable set therefore, which may be implemented in the system of FIG. 3 and use any of the servicing regime embodiments discussed herein.

Dialyzer 40 is an example of a component that when used with certain hemodialysis systems is a single component and when used with other hemodialysis systems is a multi-treatment component. For systems requiring multiple uses of dialyzer 40, the dialyzer may be subject to clearance and/or integrity tests as discussed above. Similarly, FIG. 4 illustrates one embodiment for a peritoneal dialysis system 210, which may operate to use a disposable set only once or over multiple treatments. Peritoneal dialysis system 210 includes a peritoneal dialysis machine or cycler 212, which operates a disposable set 220. Disposable set 220 includes a disposable pumping cassette 222, which may include a hard plastic middle section 224 sealed on both surfaces by a flexible plastic sheet, diaphragm or membrane 226. Hard plastic middle section 224 defines pump and valve chambers, rigid fluid flow paths and ports for mating with tubing 228 of disposable set 220 and tubing 232 associated with solution bags 230. Tubing 228 in one embodiment runs to the patient, a drain and a heater bag 234 of disposable set 220.

In use, heater bag 234 is placed on a heating tray 214 of cycler 212. When not in use, as illustrated in FIG. 4, a user interface 216 of cycler 212 folds down into heating tray 214 and is covered by a lid of cycler 212. In use, disposable pumping cassette 222 is loaded against a pump and valve actuation area 218 of cycler 212. A door including an inflatable bladder and push plate 240 is closed onto and pressurized to press disposable pumping cassette 222 into operation with pump and valve actuation area 218 of cycler 212. In an embodiment, the fluid pumps and valves of disposable pumping cassette 222 are actuated pneumatically. Alternatively, the fluid pumps and valves of disposable pumping cassette 222 are actuated electomechanically, e.g., via peristaltic pumping.

Disposable set 220 is in one embodiment a single use or treatment item and is discarded after the single use. In another embodiment, disposable set 220 is reused multiple times. For example, disposable set 220 may be disinfected chemically and/or via radiation, e.g., via ultraviolet light, between uses. When reused, the soft and hard limits of the present disclosure may be employed. For example, disposable pumping cassette 222, tubing 228, 232, solution bags 230 and heater bag 234 may each be subjected to one or more common or individualized integrity test after each treatment. A soft limit could be triggered for example when measured integrity air pressure drops a certain amount within a certain time period. The disposable set 220 may still be reused after soft limit is reached, but the patient or user is put on notice that the disposable set will need to be changed soon. In another embodiment, the patient or user is told to change the disposable set when the soft limit is reached.

In another example, pumping performance is measured before, during and/or after treatment. Here, cycler 212 may expect that a pump chamber or valve chamber of disposable pumping cassette 222 should reach its end-of-stroke position within a certain period of time. Cycler 212 may sense an end-of-stroke position by looking for a pressure spike that occurs when membrane 226 bottoms-out against a pump or valve chamber wall of hard plastic middle section 224. As membrane 226 becomes used more and more over multiple treatments, it may tend to wear out, such that a longer period of time is needed for membrane 226 to bottom-out at the end-of-stroke position to be seen for the same applied operating pressure. Here, a soft limit may be set to trigger when membrane 226 performance has degraded by, for example, 20 percent. At such time, the patient or user may be told to change disposable set 220 or to be prepared to change disposable set 220 soon. The end-of-stroke performance measurement may be done using positive pressure to bottom membrane 226 out into hard plastic middle section 224, using negative pressure to bottom membrane 226 out outwardly against pump and valve interface 218, or both.

In an electromechanical example, e.g., when a peristaltic pump is used, the performance metric may be output pressure. It may be expected that at a certain a certain pressure output is provided at a certain rotational pump speed of the peristaltic pump. When pressure output lessens due to the peristaltic pump tube wearing out over multiple treatments, a soft limit, e.g., twenty percent pressure loss, may be triggered. At such time, the patient or user may be told to change the disposable set or to be prepared to change the disposable set soon. The peristaltic pump performance measurement may be done using positive pressure output of the electromechanical pump, using negative pressure input to the electromechanical pump, or both.

In another example, the ability of a valve of disposable pumping cassette 222 to stay closed when under positive pressure may be evaluate. Here, a valve of cassette 222 when primed with fluid may be closed pneumatically, e.g., under a positive pressure of five psig. The closed valve is then subjected to fluid pressure from within via an actuation of a pump chamber in fluid communication with the valve, starting e.g., at three psig and ramping up. It is expected that the valve will open when the pumping pressure exceeds the valve holding pressure of five psig. When this happens a measurable pressure drop will occur at the pump chamber as fluid may now travel through the valve. But if the measured pressure drop indicating the valve opening occurs before the valve closing pressure of five psig is reached, it may indicate an improperly seated valve or a worn out valve membrane 226. When valve holding pressure lessens, e.g., to twenty percent of the valve closing pressure for any reason, a soft limit may be triggered. At such time, the patient or user may be told to change disposable set 220 or to be prepared to change the disposable set 220 soon.

In a further example, the ability of pneumatically actuated or electromechanically driven fluid pumps to mix a solution properly is monitored. One or more conductivity sensor may be used, for example, to verify that cycler 212 (or hemodialysis machine 90) has mixed one or more concentrate in the correct proportion(s) with water purified to be suitable for whatever treatment is being performed. Here, the soft and hard limit system and methodology of the present disclosure may (but does not have to) look for weighted trends or trends over multiple days and/or treatments to determine if a soft limit has been reached. For example, if a moving average three day or treatment trend falls below a certain accuracy percentage of commanded conductivity, e.g., at or below ninety-five percent accurate, then a soft limit is reached. At such time, the patient or user may be told to change the disposable set or to be prepared to change the disposable set soon. The weighted trend allows for one or more mixing conductivity outcomes falling beneath the specified accuracy level to occur without triggering a soft limit. In a three day average trend, where the three days produce mixing conductivity accuracies of 96%, 96% and 94%, for example, the average of 95.3% remains above the accuracy limit of 95%, such that a soft limit is not triggered. But if the next day also yields a mixing conductivity accuracy of 94%, for example, then the current three day results become, 96%, 94% and 94% and produce an average of 94.7%, which does trigger a soft limit of the present disclosure. Moving averages allow for anomalies to occur in situations where anomalies typically occur, e.g., in mixing situations in which the mixture may not be perfectly homogenous, so as to not overreact and thereby prolong the life of the disposable item.

It should be appreciated that each of the examples discussed in connection with peritoneal dialysis system 210 of FIG. 4 is equally applicable to any blood cleaning modality discussed herein, e.g., one employing medical fluid delivery machine 90 and/or blood set 100. FIG. 2 for example shows a pneumatically operated blood set 100, which may be subject to pneumatic integrity and performance tests, pumping output tests, and/or mixing accuracy tests as just described.

Figure 5:
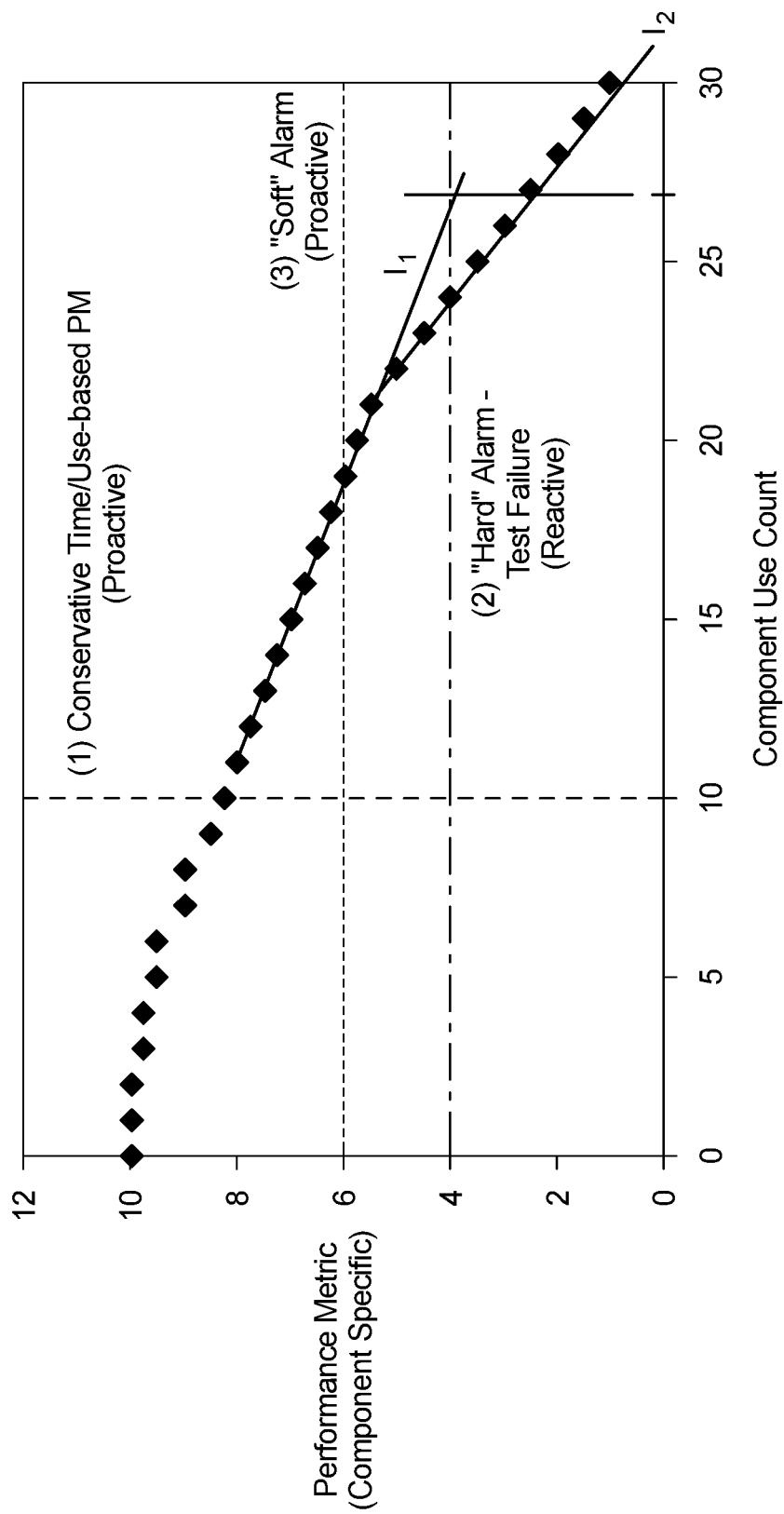
FIG. 5 is a plot illustrating one embodiment for a servicing regime of the present disclosure.

Referring now to FIG. 5, a servicing regime as illustrated may be implemented at the computers of service personnel 132a to 132 (FIG. 3), at the computers of doctors or clinicians 126a to 126n (FIG. 3), and/or on machines 90 (FIG. 3) and/or 212 (FIG. 4) themselves. FIG. 5 illustrates an embodiment of the servicing regime of the present disclosure. Component use count is provided along the x-axis, while a performance metric for the component is provided along the y-axis. In the illustrated example, better performance is indicated by a larger number along the y-axis, e.g., fluid flowrate through an ultrafilter 80 (FIG. 1).

As illustrated in FIG. 5, in a first component replacement scenario (1), the component, e.g., ultrafilter 80, is replaced after a certain number of treatments or after a certain number of hours in use. This scenario is disadvantageous because to make sure that the component is not used after failure, the treatment number limit or hours of use limit has to be set low with a safety factor to account variabilities in each of the components analyzed under this scenario.

As illustrated in FIG. 5, in a second component replacement scenario (2), the component is replaced reactively after it fails. This scenario is also disadvantageous because replacement is now a necessity before another treatment can be run, which may take the machine offline while a new component is retrieved. Also, the component may fail during a treatment, potentially creating a safety issue. Further, the component failure may leave a negative impression with the patient, doctor and/or clinician concerning machine 90 or cycler 212.

As illustrated in FIG. 5, in the servicing regime of the present disclosure, a soft limit is set at some safety factor above the hard limit, which indicates a component failure performance along the y-axis. The soft limit as illustrated will generally allow for a greater number of treatments or hours of operation than the conservative time or use based limit. Even if the component is replaced at the soft limit, there is likely a prolonging of component life and a decrease in component and servicing cost over time relative to the conservative limit.

It is however not required to replace the component when the soft limit is reached. The soft limit instead puts relevant people on notice that component replacement is immanent. The soft limit is one way according to the present disclosure to provide an indication of how well the component is performing relative to the component replacement limit.

There are at least two ways to configure the x-axis of FIG. 5, namely, to make the units represent component (i) use count (e.g., number of treatments) or (ii) component use time (e.g., hours of service actually performed). There are also at least two general ways in which the performance metric along the y-axis may be measured. In a first way, the performance metric of a machine component is measured by measuring an output of the component. In one example, ultrafilter 80 may be evaluated by measuring an output flowrate of purified fluid from the ultrafilter at a set inlet fluid pressure to the ultrafilter. In a second way, the performance metric of a machine component is measured by testing the component. In one example, ultrafilter 80 may be evaluated via pressure testing, e.g., a pressure decay test. Both the output and testing metrics evaluate the porous hollow fiber membranes of ultrafilter 80. The flowrate metric checks to see if the porous hollow fiber membranes are clogged or blocked, while the pressure test metric checks to see if the porous hollow fiber membranes are leaking, e.g., if there is a tear in one or more of the membranes.

It is therefore contemplated to track two or more performance metrics, e.g., via database or via a graph such as that of FIG. 5, for the same component, e.g., ultrafilter 80. An algorithm is then programmed to signal when either of the performance metrics reaches the respective soft limit or the respective hard limit. That is, the first metric to fail, or begin to fail, controls the replacement of the component.

Both performance metric analyses, component output and component testing, may be performed one or more time for each treatment using medical fluid delivery machine 90 or cycler 212. For example, the pressure testing of ultrafilter 80 may be performed before each treatment to make sure ultrafilter 80 is not leaking. The output of ultrafilter 80 is the flowrate of fresh dialysis fluid along line 76 (FIG. 1) from the ultrafilter 80 to dialyzer 40, e.g., at a set pumping pressure provided by fresh dialysis fluid pump 64. The average flowrate for a treatment may be determined by dividing a total amount of dialysis fluid delivered to dialyzer 40 divided by the total time that dialysis fluid pump 64 is running during treatment (e.g., total treatment time less downtime for alarms, etc.). The generation of treatment performance metric data is important to monitoring the soft limits of the present disclosure and to track how well the component is performing relative to the component replacement limit. Per-treatment performance data may be uploaded to desired places of overall system 110 as discussed above and/or maintained at machine 90 or cycler 212.

The following is a non-exclusive list of components from FIGS. 1 to 4 having outputs that may be monitored as a performance metric according to FIG. 5: (i) ultrafilter of water purification unit 60 having purified water flowrate output, (ii) pump of water purification unit 60 having purified water flowrate output, (iii) pre-filter pack of water purification unit 60 having chlorine removal capability output, (iv) blood pump 30 having blood flowrate output, (v) dialyzer 40 having blood flowrate output, (vi) fresh water and concentrate pumps (not illustrated in FIG. 1) having fresh water and concentrate flowrate outputs respectively, (vii) fresh dialysis fluid pump 66 having fresh dialysis fluid flowrate output, (viii) ultrafilter 80 having fresh dialysis fluid flowrate output, (ix) dialyzer 40 having used dialysis fluid flowrate output, (x) used dialysis fluid pump 96 having used dialysis fluid flowrate output, (xi) ultrafiltrate pump (not illustrated in FIG. 1) having ultrafiltrate flowrate output, and (xii) output metrics for blood set 100 and disposable set 220.

It should be appreciated from the above list that certain outputs, such as fresh dialysis fluid flowrate, are associated with multiple components, e.g., fresh dialysis fluid pump 66 and ultrafilter 80. As discussed in detail below, it is contemplated to develop and maintain characteristic performance curves for different components of medical fluid delivery machine 90 or cycler 212. The characteristic performance curves for two different components associated with the same output may be different enough such that the actual performance curve dictates which component is failing. For example, the characteristic output flowrate from ultrafilter 80 may slope over time as in FIG. 5, while the characteristic output flowrate from fresh dialysis fluid pump 66 may show a sharp drop off in performance. If the actual fresh dialysis fluid flowrate deterioration matches one of the characteristic fresh dialysis fluid flowrate deteriorations, then the corresponding component may be assumed to be the culprit. Alternatively, a service person may prepare to replace either component, e.g., dialysis fluid pump 66 or ultrafilter 80, whichever is needed when servicing is performed.

The following is a non-exclusive list of components from FIGS. 1 to 4 having outputs that may be tested as a performance metric according to FIG. 5: (i) pressure test of ultrafilter of water purification unit 60, (ii) test of chlorine sensor of water purification unit 60 using known dechlorinated water and/or water of known amount of chlorine, (iii) a test of any or all conductivity sensors in dialysis fluid circuit 70 of FIG. 1 using fluid of zero conductivity and/or fluid of known conductivity, (iv) a test of any or all pressure sensors (e.g., pneumatic pressure sensors) associated with blood circuit 20 and dialysis fluid circuit 70 of FIG. 1 using test fluid (e.g., air) at known pressure, (v) leak test (e.g., pressure decay test) of any or all valves (e.g., pneumatic valves) associated with blood circuit 20 and dialysis fluid circuit 70 of FIG. 1, (vi) a pressure test (e.g., pressure decay) of any fluid line section associated with blood circuit 20 and dialysis fluid circuit 70 of FIG. 1, wherein the section includes a fluid pump chamber in between to fluid valves defining the segment and enabling the pump chamber to fluidly pressurize the line segment, (vii) a pressure test (e.g., pressure decay) of ultrafilter 80, (viii) a fiber bundle test known to those of skill in the art to assess the clearance ability of the membranes of dialyzer 40, (ix) a conductivity or sodium spike test (e.g., upstream and downstream of dialyzer 40) known to those of skill in the art to assess the clearance ability of the membranes of dialyzer 40, (x) a test of air detectors 22a and 22v via passing a liquid known to have entrained air through the sensors, and (xi) tests performed on blood set 100 and disposable set 220.

In one embodiment, when the performance of a component reaches a soft limit as illustrated in FIG. 5, the component is placed in a "watch mode". Watch mode components may be communicated to necessary individuals in a variety of ways. FIG. 6 illustrates a watch mode screen 242, which may be provided on wireless tablet user interface 122 (FIG. 3) of machine 90 (or screen 216 of cycler 212) at clinics 126a to 126n that would rather a service person or clinician have access to the information at the machine itself rather than remotely at a computer. Watch mode screen 242 is specific to its machine 90 or cycler 212 in one embodiment. Watch mode screen 242 lists each component of machine 90 or cycler 212 whose performance data or test data has deteriorated to the soft limit illustrated in FIG. 5. For each component, the example watch mode screen 242 of FIG. 6 provides: (i) the name of the component, (ii) the location of the component in machine 90 or cycler 212 (e.g., specifying which of multiple ones of the same component), (iii) product ordering or replacement number, (iv) a projected number of uses or hours before the replacement limit, (v) a projected replacement limit date, and (vi) a link to a chart or graph of the performance data or test data (e.g., also showing projected replacement limit date) like FIG. 5.

In the illustrated embodiment, components are ordered by replacement urgency, in which components having the greatest urgency are listed at the top. Screen 242 may be provided by machine 90 (or screen 216 of cycler 212) as a flag or alert to prompt the clinician or service person to review the soft limit data. Alternatively, screen 242 is provided as part of a service mode of machine 90 (or screen 216 of cycler 212), which the clinician or service person is instructed to check routinely.

The projected replacement limit number of uses or hours is provided in one embodiment by determining the slope of the line from the last two data points and extending the line from the last data point at the determined slope for future intervals along the x-axis of the chart, and determining where the extended line hits the horizontal replacement limit line (FIG. 5), and from there estimating how many additional treatments or service hours may be available before component failure occurs. The estimated additional treatments or service hours may be converted additionally into a projected future date of mandatory component replacement if it is known how many treatments or service hours are performed per day, taking into account weekends, holidays, off days, etc.

Using a linear slope over the last two data points may be found to be too reactionary. It is accordingly contemplated to alternatively fit a curve mathematically to all relevant data points. For example, as illustrated in FIG. 5, a curve could be fitted to all performance metric data points that are a predetermined percentage above the soft limit output (output of 6), for example, beginning at the output of 8 (y-axis), which occurs at ten or eleven uses (x-axis). Once the actual output hits the soft limit output (at nineteen component uses), the component is added to watch mode screen 242 and a predicted number of additional component uses until failure is provided. The slope of the line $l_1$ in FIG. 5 between ten and nineteen uses predicts about twenty-seven total uses before failure. However, once on the watch list, the mathematical curve taking to account the performance metric output at twenty-one and twenty-two uses adjusts the prediction to failure (output of 4) via line $l_2$ to be twenty-four total uses. At twenty-two uses, the service person or other authorized personnel therefore knows to change the component quickly.

Referring now to FIG. 7, an example watch mode screen 244 shown at the computers of service personnel 132a to 132n and/or at the computers of hospitals or clinics 126a to 126n is illustrated. Service personnel 132a to 132n and hospitals or clinics 126a to 126n monitor multiple machines 90 or cyclers 212. Watch mode screen 244 accordingly lists each machine under the control of service personnel 132a to 132n or hospitals or clinics 126a to 126n having at least one component with performance or test data at or below the soft limit. For each listing, example watch mode screen 244 provides: (i) location (e.g., facility, room at facility, or patient's home), (ii) machine identity/type, (iii) number of components at soft limit for that machine, (iv) shortest number of uses/hours to failure, and (v) earliest date of failure. Again, the watch mode screen 244 listings may be ordered by replacement urgency in which machines 90 or cyclers 212 with components having the greatest urgency are listed at the top.

FIG. 7 illustrates different types of machines under one clinic or hospital, e.g., hemodialysis machines ("HD"), peritoneal dialysis machines ("PD"), infusion or large volume pumps ("LVP"), and CRRT machines. Note that for the location column, a clinic site may be listed for in-center machines 90 or cyclers 212, while a patient's name (e.g., J. Doe, P. Shent) may be listed for a home machine 90 or cycler 212.

Watch made screen 244 may be provided as a flag or alert file at the computer of clinic 126a to 126n or service personnel 132 as a prompt. Alternatively, the clinician, service person or other authorized person may be tasked with checking watch made screen 244 routinely. When the service person, clinician or other authorized person selects one of the machine listings on watch mode screen 244, a screen the same as or similar to watch mode screen 242 discussed above at FIG. 6 appears on clinician computer 126a to 126n or service person computer 132, showing each component of the selected machine with performance or test data at or below the soft limit, including all the information provided by screen 242 discussed above. The service person, clinician or other authorized person proceeds accordingly.

Figure 8:
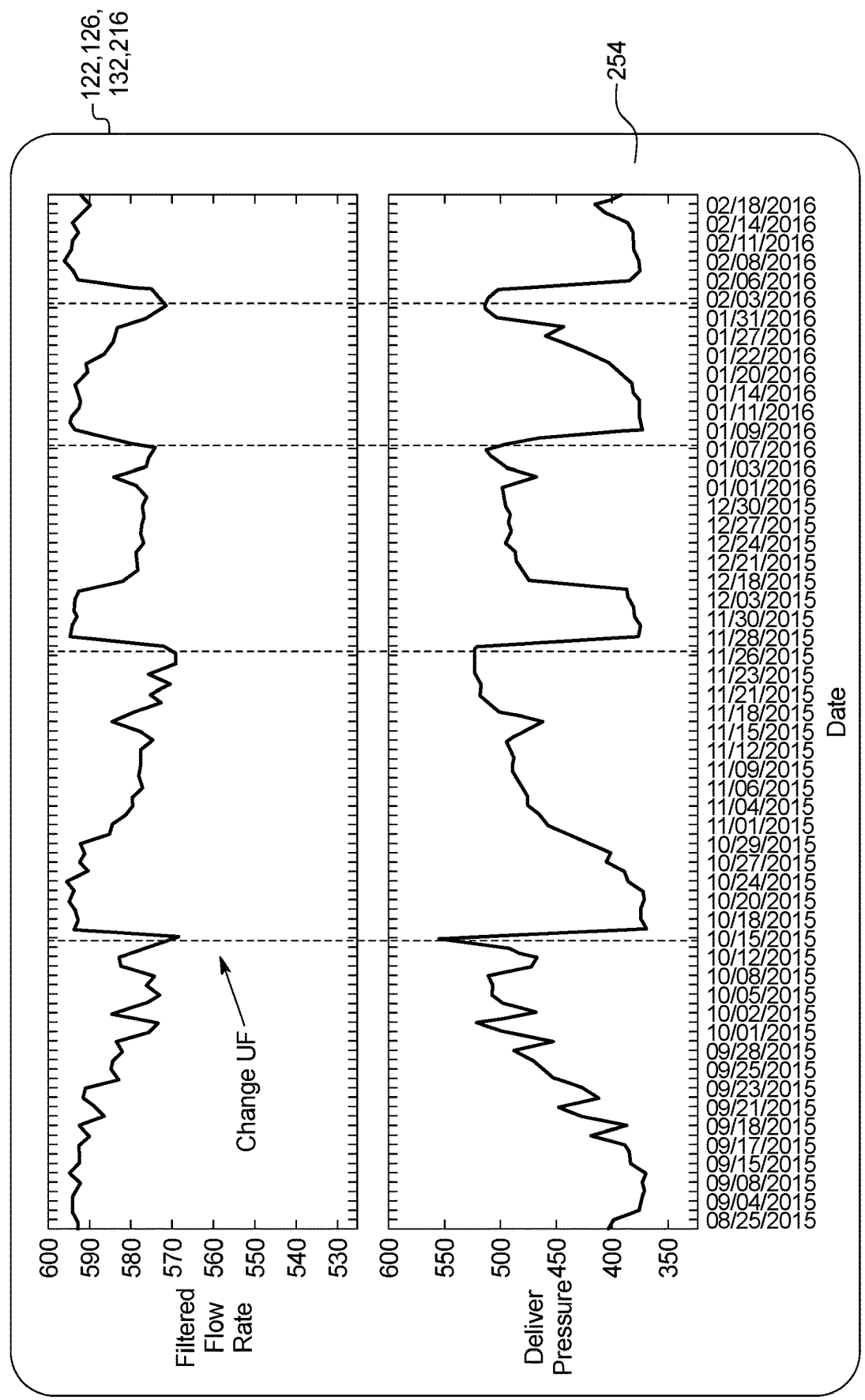
FIG. 8 is a screen shot showing charted data for a machine component over multiple replacement cycles.

It is another feature of the present disclosure to analyze and track performance or test data over multiple cycles in an attempt to observe trends in the data. For example, FIG. 6 shows that watch mode screen 242 for a particular machine 90 (or screen 216 of cycler 212) may provide trend buttons for components that are replaced frequently, such as an ULTRAFILTER TRENDS button 246, a DIALYZER TRENDS button 248, a PRESSURE SENSOR TRENDS button 250, and a PNEUMATIC VALVE TRENDS button 252. Selecting any of the trends buttons, e.g., ULTRAFILTER TRENDS button 246 brings the user to a dedicated trends screen, such as ultrafilter trends screen 254 of FIG. 8, which may be displayed on any of machine user interface or tablet 122, screen 216 of cycler 212, the computer of a hospital or clinic 126, or the computer of a service person 132.

Ultrafilter trends screen 254 illustrates four different consecutive instances in which ultrafilter 80 (FIG. 1) was replaced (vertical dashed line) on the same machine 90 or cycler 212 and in one embodiment for a same patient. For the same date, an upper plot shows flowrate output, while a lower plot shows driving pressure. A service person, clinician or other user viewing ultrafilter trends screen 254 of FIG. 8 gets a sense of (i) how long on average that ultrafilter 80 lasts for a particular machine treating a particular patient, (ii) what the flowrate curve looks like just before ultrafilter 80 replacement, and (iii) what the driving pressure curve looks like just before ultrafilter 80 replacement. Viewing the plots at the furthest right of screen 254, from the dates Feb. 6, 2016 to Feb. 18, 2016, the user can see that all three indicators, namely, duration in service, flowrate output, and drive pressure required, indicate that the present ultrafilter 80 is currently performing well and that replacement is not immanent. It is contemplated that similar conclusions may be made viewing performance trends for a dialyzer via DIALYZER TRENDS button 248, a pressure sensor via PRESSURE SENSOR TRENDS button 250, and a pneumatic valve via PNEUMATIC VALVE TRENDS button 252 illustrated in FIG. 6.

FIG. 6 provides trends buttons for a single machine 90 or cycler 212. If machine 90 or cycler 212 is provided at home, then the trends buttons will also be for a single patient. It is therefore expressly contemplated for system 10 and the servicing regimes of the present disclosure to develop trends for specific patients, including tracking which components the patient is consuming most frequently and how often. Comparing one patient's trends to another may shed light on why certain components wear out faster for certain patients. Such analysis may lead to a determination that certain types of treatment or treatment prescriptions, e.g., more frequent treatments, longer treatments, higher temperature treatments, etc., lead to more frequent replacement of certain machine components.

If machine 90 or cycler 212 is provided at a clinic 126a to 126n, then the trends buttons will likely be for multiple patients. Analyzing data for a machine treating multiple patients tends to take individual patients out of the equation. This data is good for system 10 to compare two different makes of the same machine, e.g., different manufacturers or older versus newer machines. Such analysis may lead to a determination that certain types makes or brands of machine 90 or cycler 212 lead to more frequent replacement of certain machine components.

FIG. 7 illustrates buttons that allow for the user to see combined data from like machines (HD, PD, LVP, CRRT) across a whole clinic, across multiple clinics, or across an entire manufacturer's platform. An ULTRAFILTERS AVERAGED button 256 may for example provide averaged replacement durations and split such data by ultrafilter brand if different ones exist and/or by any other desired feature, such as average operating pressure, dialysis fluid temperature, etc. Similar information may be provided for dialyzers 40 via a DIALYZERS AVERAGED button 258 and may additionally include analysis in light of blood flowrate.

Averaging may also be performed and displayed for other desirable components, such as pressure sensors, pneumatic valves, and pump and valve diaphragms.

FIG. 7 also illustrates a REORDER NOW button 260, which shows the user which components should be reordered promptly and why. Suppose lead time and minimum order quantity for ultrafilter 80 are four weeks and 100 pieces, respectively, and that there are twenty ultrafilters currently in stock. Assume also that the service regime of the present disclosure shows on average that three ultrafilters 80 are replaced each week, but that the present soft limit list shows that six ultrafilters 80 are currently at their soft limit, with five or less days until projected mandatory replacement. The estimate for the next four weeks (one lead time period) is therefore that six (soft limit for first week)+three (average for the second week)+three (average for the third week)+three (average for the fourth week) or fifteen ultrafilters 80 will be consumed. The service regime may be programmed to alert the user via the REORDER NOW button 260 whenever the four week (one lead time period) projection shows five or fewer ultrafilters 80 remaining in stock. Pressing REORDER NOW button 260 thereby informs the user to reorder ultrafilter 80 and provides reasoning therefore in one embodiment.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A medical fluid delivery system comprising:
   a medical fluid delivery machine including at least one component, an air pressure source, and a pressure sensor, wherein the at least one component is subjected to a pressure decay test in which the at least one component is pressurized via air pressure from the air pressure source for producing associated output data provided by at least one of the pressure sensor or the at least one component, the output data being related to an operation or a performance of the at least one component for a medical fluid delivery treatment;
   at least one component replacement limit for the at least one component;
   at least one component soft limit for the at least one component, the at least one component soft limit indicative of a degradation in the operation or the performance of the at least one component; and
   a computer programmed to
      store the at least one component replacement limit and the at least one component soft limit,
      analyze the output data in relation to the at least one component replacement limit and the at least one component soft limit, and
      provide an indication of how well the at least one component is performing relative to the at least one component replacement limit, the indication including whether the at least one component is operating between the at least one component soft limit and the at least one component replacement limit.

2. The medical fluid delivery system of claim 1, wherein the medical fluid delivery machine includes a display device, the computer provided by a control unit of the medical fluid delivery machine, and wherein the indication is displayed by the display device of the medical fluid delivery machine.

3. The medical fluid delivery system of claim 1, wherein the computer is a remote computer having a display device, the medical fluid delivery machine in data communication with the remote computer via at least one server, and wherein the indication is displayed by the display device of the remote computer.

4. The medical fluid delivery system of claim 1, wherein the indication-includes a number of uses or treatments remaining for the at least one component before reaching the at least one component replacement limit.

5. The medical fluid delivery system of claim 1, wherein the computer is programmed to generate at least one component performance graph showing the at least one component performing relative to the at least one component soft limit and the at least one component replacement limit.

6. The medical fluid delivery system of claim 1, wherein the computer is programmed to generate an estimate of when component performance will reach the at least one replacement limit when the at least one component is performing between the at least one component soft limit and the at least one component replacement limit.

7. The medical fluid delivery system of claim 1, wherein the computer is a remote computer, the medical fluid delivery machine is in data communication with the remote computer via at least one server, and the at least one component includes two or more components, and which includes a file provided by the computer indicating which of the two or more components is performing between the at least one component soft limit and the at least one component replacement limit.

8. The medical fluid delivery system of claim 1, wherein the computer is a remote computer, the medical fluid delivery machine is in data communication with the remote computer via at least one server, and the at least one component includes two or more components, and which includes a file provided by the computer indicating which of the two or more components of the medical fluid delivery machine and other medical fluid delivery machines are performing between the at least one component soft limit and the at least one component replacement limit.

9. The medical fluid delivery system of claim 1, wherein the computer receives the output data associated with the at least one component after each treatment performed by the medical fluid delivery device.

10. The medical fluid delivery system of claim 1, wherein the associated output data includes a flowrate, and wherein at least one of the component replacement limits is a component replacement flowrate.

11. The medical fluid delivery system of claim 10, wherein the at least one component includes (i) a filter, the flowrate being a flowrate downstream of the filter, (ii) a medical fluid delivery pump, the flowrate being a flowrate downstream of the medical fluid delivery pump, or (iii) a disposable item, the flowrate being a flowrate downstream of the disposable item.

12. A medical fluid delivery system comprising:
   a medical fluid delivery machine including at least one component, an air pressure source, and a pressure sensor, wherein the at least one component is subjected to a pressure decay test in which the at least one component is pressurized via air pressure from the air pressure source to produce test data provided by at least one of the pressure sensor or the at least one component;

at least one component replacement limit for the at least one component; and a computer programmed to store the at least one component replacement limit and to analyze the test data to provide an indication of how well the at least one component is testing relative to the at least one component replacement limit.

13. The medical fluid delivery system of claim 12, wherein the at least one component includes (i) a filter including a filtering membrane, the pressure decay test testing the filtering membrane, (ii) a fluid delivery component, the pressure decay test testing the fluid delivery component for a leak, (iii) a disposable component, the pressure decay test testing the disposable component for a leak, or (iv) a fluid line, the pressure decay test testing the fluid line for a leak.

14. The medical fluid delivery system of claim 12, wherein the medical fluid delivery machine includes a display device, the computer provided by a control unit of the medical fluid delivery machine, and wherein the indication is displayed by the display device of the medical fluid delivery machine.

15. The medical fluid delivery system of claim 12, wherein the computer is a remote computer having a display device, the medical fluid delivery machine in data communication with the remote computer via at least one server, and wherein the indication is displayed by the display device of the remote computer.

16. The medical fluid delivery system of claim 12, wherein the computer receives the test data associated with the at least one component after each treatment performed by the medical fluid delivery device.

17. The medical fluid delivery system of claim 12, wherein the at least one component includes a sensor for the medical fluid delivery machine, the test analyzing an output from the sensor.

18. The medical fluid delivery system of claim 17, wherein the sensor is the pressure sensor, a conductivity sensor, or a temperature sensor.

19. The medical fluid delivery system of claim 12, which includes at least one component soft limit in addition to the at least one component replacement limit stored by the computer, the at least one component soft limit indicative of a degradation in an operation or a performance of the at least one component, wherein the indication of how well the at least one component is testing relative to the at least one component replacement limit includes whether component testing performance is between the at least one component soft limit and the at least one component replacement limit.

20. The medical fluid delivery system of claim 19, wherein the computer is a remote computer, the medical fluid delivery machine in data communication with the remote computer via at least one server, and which includes a file provided by the computer indicating which of the at least one component of the medical fluid delivery machine and other medical fluid delivery machines are performing between the at least one component soft limit and the at least one component replacement limit.

21. The medical fluid delivery system of claim 19, wherein the computer is programmed to generate at least one testing performance graph showing the at least one component testing performance relative to the at least one component soft limit and the at least one component replacement limit.

22. The medical fluid delivery system of claim 19, wherein the computer is programmed to generate an estimate of when the component testing performance will reach the at least one replacement limit when the component testing performance is between the at least one component soft limit and its component replacement limit.

23. The medical fluid delivery system of claim 19, wherein the computer is a remote computer, the medical fluid delivery machine in data communication with the remote computer via at least one server, and which includes a file provided by the computer indicating which of the at least one component is performing between the at least one component soft limit and the at least one component replacement limit.

24. A medical fluid delivery system comprising:

a medical fluid delivery machine including at least one component, an air pressure source, and a pressure sensor, wherein the at least one component is subjected to a pressure decay test in which the at least one component is pressurized via air pressure from the air pressure source to produce associated output data and associated test data that are related to an operation or a performance of the at least one component, the associated output data and the associated test data being produced by at least one of the pressure sensor or the at least one component;

at least one component output replacement limit for the at least one component;

at least one component soft limit for the at least one component, the at least one component soft limit indicative of a degradation in the operation or the performance of the at least one component;

at least one component testing replacement limit for the at least one component; and a computer programmed to store the at least one component output replacement limit, the at least one component soft limit, and the at least one component testing replacement limit, analyze the output data in relation to the at least one component output replacement limit and the at least one component soft limit, analyze the test data in relation to the at least one component testing replacement limit, provide a first indication of how well the at least one component is performing relative to the at least one component output replacement limit, the first indication including whether the at least one component is operating between the at least one component soft limit and the at least one component output replacement limit, and provide a second indication of how well the at least one component is testing relative to the at least one component testing replacement limit.

25. A medical fluid delivery system comprising:

a medical fluid delivery machine including a component, an air pressure source, and a pressure sensor, wherein the component is subjected to a pressure decay test in which the component is pressurized via air pressure from the air pressure source to produce at least one of associated output data or associated test data that are related to an operation or a performance of the component, the at least one of associated output data or associated test data being produced by at least one of the pressure sensor or the component;

at least one of (i) a component output replacement limit and a component output soft limit for the component or (ii) a component testing replacement limit or a component testing soft limit for the component; and a computer programmed to
- store at least one of (i) or (ii),
- if (i) is stored, analyze the output data to provide a first indication of how well the component is performing relative to the component output replacement limit and the component output soft limit, and
- if (ii) is stored, analyze the test data to provide a second indication of how well the component is testing relative to the component testing replacement limit and the component testing soft limit.

\* \* \* \* \*